United States Patent [19]

Bolhofer et al.

[11] 4,229,456

[45] Oct. 21, 1980

[54] SUBSTITUTED NAPHTHYRIDINONES AND PROCESSES FOR THEIR PREPARATIONS

[75] Inventors: William A. Bolhofer, Frederick; Edward J. Cragoe, Jr., Lansdale; Jacob M. Hoffman, Jr., North Wales, all of Pa.

[73] Assignee: Merck & Co., Inc., Rahway, N.J.

[21] Appl. No.: 954,388

[22] Filed: Oct. 23, 1978

Related U.S. Application Data

[62] Division of Ser. No. 816,617, Jul. 18, 1977, Pat. No. 4,133,885.

[51] Int. Cl.$^3$ .................. C07D 403/02; A61K 31/44
[52] U.S. Cl. ................... 424/256; 544/127; 546/122; 546/123; 546/193; 424/248.5; 424/248.57
[58] Field of Search .............. 546/122, 123, 193; 424/256, 248.5, 248.57; 544/127

[56] References Cited

U.S. PATENT DOCUMENTS

| | | | |
|---|---|---|---|
| 3,429,887 | 2/1969 | Lesher | 546/123 X |
| 3,590,036 | 6/1971 | Lesher et al. | 546/123 X |
| 3,673,193 | 6/1972 | Lesher et al. | 546/123 OR |
| 4,133,885 | 1/1979 | Bolhofer et al. | 424/256 OR |

OTHER PUBLICATIONS

Hawes et al. (I), J. Chem. Soc. C (Org.), 1966, pp. 315 to 321.
Hawes et al. (II), J. Chem. Soc. C (Org.), 1967, pp. 1564 to 1567.
Allen, Chem. Reviews, vol. 47, p. 295 (1950).
Oae, Organic Chemistry of Sulfur, p. 196, Plenum Press (NY) 1977.
English et al., Principles of Organic Chemistry, p. 334, McGraw-Hill Book Co. Inc., NY (1949).
Klingsberg, Pyridine and Its Derivatives, Part Three, p. 651, Interscience Pulbishers (1962).

*Primary Examiner*—John D. Randolph
*Attorney, Agent, or Firm*—David L. Rose; Harry E. Westlake

[57] ABSTRACT

Organic chemical compounds based upon the naphthyridine molecule are disclosed which have potent gastric secretion inhibitory properties. The naphthyridinone is substituted with a substituted amino alkyl group at the 1-position, and variously substituted at the remaining positions. The compounds have profound effects on the inhibition of gastric secretions in the gastrointestinal tract, and compositions for such uses are also disclosed.

7 Claims, No Drawings

SUBSTITUTED NAPHTHYRIDINONES AND PROCESSES FOR THEIR PREPARATIONS

CROSS REFERENCE TO RELATED APPLICATIONS

This application is a divisional application of our application U.S. Ser. No. 816,617, filed July 18, 1977, now U.S. Pat. No. 4,133,885, issued on Jan. 9, 1979.

BACKGROUND OF THE INVENTION

Excess secretion of gastric acid can cause indigestion and stomach distress and, if prolonged, may result in ulcer formation. Treatment of excess secretion of gastric acid has heretofore consisted mainly of a bland diet, abstinence from certain foods and the use of antacids to neutralize the gastric acid after it is secreted into the stomach. An improved method of treatment would result from the inhibition of gastric acid secretion. It is thus an object of the present invention to provide compounds which inhibit gastric acid secretion. Another object is to provide methods for the preparation of these compounds. A further object is to provide pharmaceutical formulations for the administration of these compounds. Still another object is to provide a method to inhibit gastric secretion. These and other objects of the present invention will become apparent from the following description.

DESCRIPTION OF THE INVENTION

The compounds of the instant invention are best described by reference to the following structural formula:

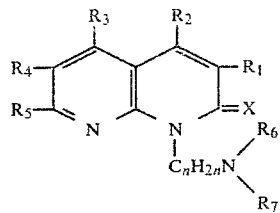

wherein X is sulfur or oxygen;

n is an integer of from 2 to 6 such that the length of the carbon chain connecting the two nitrogen atoms is not less than 2;

$R_1$, $R_2$, $R_3$, $R_4$ and $R_5$ are independently hydrogen, loweralkyl, loweralkoxy, amino, haloloweralkyl or phenyl; or any two adjacent substituents may be joined to form a benzo substituent;

$R_6$ and $R_7$ are independently hydrogen, loweralkyl, phenylloweralkyl, N-loweralkylcarbamoyl, N-loweralkylthiocarbamoyl, or $R_6$ and $R_7$ may be joined to form a morpholine ring; or $R_6$ and $R_7$ may be an alkylene linkage of 4 or 5 carbon atoms to form a pyrrolidine or piperidine ring which may be substituted with loweralkyl, oxo or benzo substituents; and the broken line in the 3,4 position of the naphthyridine molecule indicates that the bond may be either a single or a double bond provided that when n is 2, $R_3$, $R_5$, $R_6$ and $R_7$ are all methyl groups, X is oxygen, and the 3,4-position is unsaturated, at least one of $R_1$, $R_2$ or $R_4$ is other than hydrogen.

The compounds of this invention may be isolated and used as the free base or as a pharmaceutically acceptable acid addition salt. Such salts are formed by reaction of the free base with the desired inorganic or organic acid. The salts are prepared using methods known to those skilled in this art. Exemplary inorganic acids are hydrohalic acids such as hydrochloric or hydrobromic, or other mineral acids such as sulfuric, nitric, phosphoric and the like. Suitable organic acids are maleic, fumaric, tartaric, citric, acetic, benzoic, succinic, isethionic and the like.

In addition, the quaternary salts formed with the free base compounds of the foregoing structural formula and a loweralkyl halide are also considered as part of this invention. The preferred salts are prepared from loweralkyl iodides, especially methyl iodide.

In the instant specification the term "lower-alkyl" is intended to include those alkyl groups of either straight or branched configuration which contain from 1 to 6 carbon atoms. Exemplary of such alkyl groups are methyl, ethyl, propyl, isopropyl, butyl, tertiary butyl, pentyl and the like.

The term "loweralkoxy" is intended to include those alkoxy groups of either straight or branched configuration which contain from 1 to 6 carbon atoms. Exemplary of such alkyl groups are methoxy, ethoxy, propoxy, isopropoxy, butoxy, tertiary butoxy, sec butoxy, pentoxy and the like.

The "haloloweralkyl" group is defined as a loweralkyl group with 1, 2 or 3 halo substituents.

The term "halo" or "halogen" is intended to include the halogen atoms fluorine, chlorine, bromine and iodine.

The "N-loweralkylcarbamoyl" and "N-loweralkyl thiocarbamoyl" groups are respectively visualized as follows:

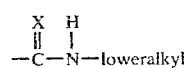

PREFERRED EMBODIMENTS OF THE INVENTION

The preferred embodiments of the instant invention are realized in the foregoing structural formula wherein:

X is oxygen;

n is 2, indicating an ethylene linkage;

the 3,4 bond in the naphthyridine molecule is a double bond;

$R_1$, $R_2$ and $R_4$ are independently hydrogen or loweralkyl; $R_3$ and $R_5$ are independently hydrogen, loweralkyl, loweralkoxy, trifluoromethyl or amino;

$R_6$ and $R_7$ are independently hydrogen or loweralkyl; provided that when $R_3$, $R_5$, $R_6$ and $R_7$ are all methyl groups at least one of $R_1$, $R_2$ or $R_4$ is other than hydrogen.

Further preferred embodiments of this invention are realized when:

X is oxygen;

n is 2, indicating an ethylene linkage;

the 3,4 bond in the naphthyridine molecule is a double bond;

$R_1$, $R_2$ and $R_4$ are hydrogen;

$R_3$ and $R_5$ are independently hydrogen, methyl or ethyl;

$R_6$ and $R_7$ are independently hydrogen, methyl, ethyl, propyl or isopropyl provided that when $R_3$ and $R_5$ are both methyl, one of $R_6$ and $R_7$ is other then methyl.

The compounds of the present invention wherein X is oxygen are prepared by reacting a substituted 2,6-diamino pyridine with a substituted 1,3-alkanedione; converting the 2-amino naphthyridine thus prepared to the 1-unsubstituted naphthyridin-2-one by a diazotization-hydrolysis, and then alkylating at the 1-position with the substituted amino alkyl group. The reaction is outlined in the following reaction scheme:

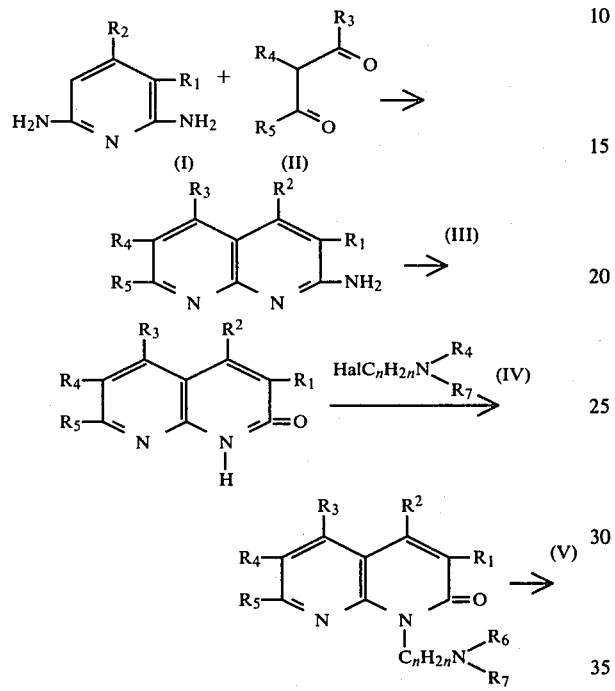

wherein $R_1$, $R_2$, $R_3$, $R_4$, $R_5$, $R_6$, $R_7$ and n are as previously defined, and Hal is a halogen.

In the first step of the reaction, an appropriately substituted 2,6-diamino pyridine (I) is combined with a 1,3-alkanedione (II) in phosphoric acid. In structure II, when $R_3$ is hydrogen the 1,3 alkanedione is a 3-oxoaldehyde and generally the reagent is employed in the form of a dialkylacetal. The mixture is heated at temperatures of from 75° to 110° C. for from 3 to 16 hours. The reaction mixture is then cooled and the product isolated using techniques known to those skilled in this art.

The 2-amino-1,8-naphthyridine (III) thus produced is converted to the diazonium salt with sodium nitrite in an acid, preferably trifluoroacetic acid or sulfuric acid. The diazonium salt is prepared at −5° C. or less during the addition, over a period of about 2 hours, of the sodium nitrite. The reaction mixture then is generally maintained at this temperature for an additional hour, and combined with a mixture of ice and water. The aqueous mixture is then made alkaline preferably with ammonium hydroxide, and the product 1,8-naphthyridine-2-(1H)-one (IV) isolated using known techniques.

This compound is then converted into the 1-substituted compound. The alkali metal salt of the 1-unsubstituted compound is first prepared, using an alkali metal hydride, preferably sodium hydride in an aprotic solvent. The preferred solvents are polar aprotic solvents such as dimethyl formamide or dioxane. The alkali metal salt is generally prepared at room temperature. In addition, the alkali metal salt may be prepared from an alkali metal alkoxide such as an alkali metal methoxide or ethoxide. The reaction is generally carried out with the alkali metal in an alcohol. The reaction is carried out at from room temperature to the reflux temperature of the reaction mixture. The alkali metal salt is generally not isolated but rather used in situ. A substituted amino alkyl halide is then added to the reaction mixture and it is heated at from 50° to 125° C. for from 3 to 24 hours. The product 1-substituted naphthyridine-2(1H)one (V) is isolated using known techniques.

The process for the preparation of the compounds of structure (V) wherein $R_6$ and $R_7$ are hydrogen involves the use of a 1-phthalimido alkyl intermediate (also a compound of this invention). The reaction proceeds as follows:

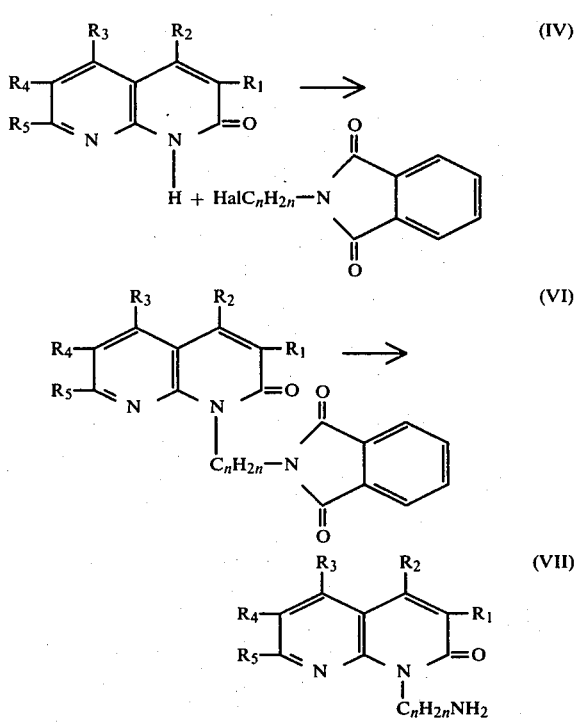

wherein Hal is a halogen.

The reaction conditions for the preparation of the phthalimido intermediate (VI) utilize the alkali metal salt as in the preparation of compound (V). The same reaction conditions are employed except that a phthalimido alkyl halide is used as the reagent.

The phthalimido intermediate (VI) is combined in a polar solvent, such as a loweralkanol, with hydrazine and heated at reflux for from 10 minutes to 2 hours, preferably for from ½ to 1 hour. The reaction mixture is cooled and acidified and the product (VII) isolated usually as the addition salt with the acidifying acid. Hydrochloric acid is preferred, however, other mineral acids are acceptable.

The compounds wherein X is sulfur are prepared from those wherein X is oxygen by treatment with phosphorus pentasulfide or from hydrogen sulfide and hydrogen chloride.

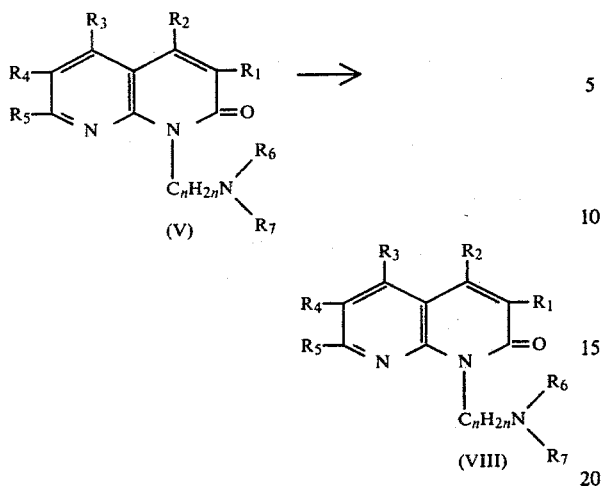

The phosphorus pentasulfide reaction takes place in methylene chloride or pyridine at from room temperature to the reflux temperature for a period of about 4 hours. Preferably the reaction is conducted at from about room temperature to 50° C. The product is isolated using known techniques.

The reaction with hydrogen sulfide and hydrogen chloride is carried out generally in an alcohol solvent at temperatures of from 0° C. to room temperature and is complete in from ½ hour to 2 days.

The compounds wherein the 3,4-position bond is a single bond are prepared from the analogous double bond compound as follows:

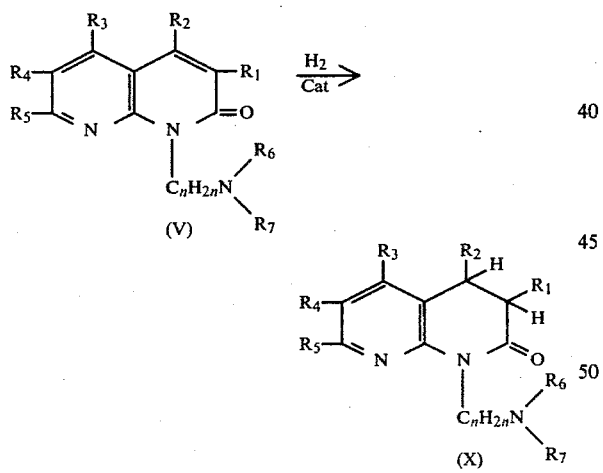

The starting material (V) is dissolved in a solvent such as a lower alkanoic acid preferably acetic acid and a catalyst such as platinum oxide is added. The mixture is then agitated under an atmosphere of hydrogen, either at atmospheric pressure or pressurized. Pressures of up to 50 pounds per square inch are utilized in the normal laboratory hydrogenation apparatus. The reaction is complete when a calculated molar quantity of hydrogen has been consumed. The reaction is generally carried out at room temperature, however, heating up to about 75° C. is acceptable.

The N-loweralkylcarbamoyl and N-loweralkylthiocarbamoyl substituents for $R_6$ or $R_7$ are prepared from the compounds wherein $R_6$ and $R_7$ are hydrogen according to the following reaction scheme:

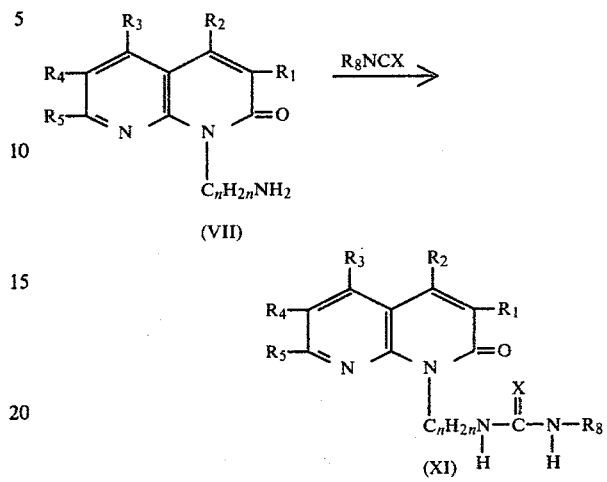

wherein $R_8$ is loweralkyl and X is oxygen or sulfur.

The compounds are prepared by reacting the primary amino compound (VII) with a loweralkyl, isocyanate or isothiocyanate. The reaction is carried out in aqueous media generally at reflux temperature. The reaction is generally complete in about 10 minutes to 1 hour at reflux and the product (XI) is isolated using known techniques.

The primary amine compound (VII) is also an intermediate for an alternate preparation of the compounds wherein $R_6$ and $R_7$ are methyl groups.

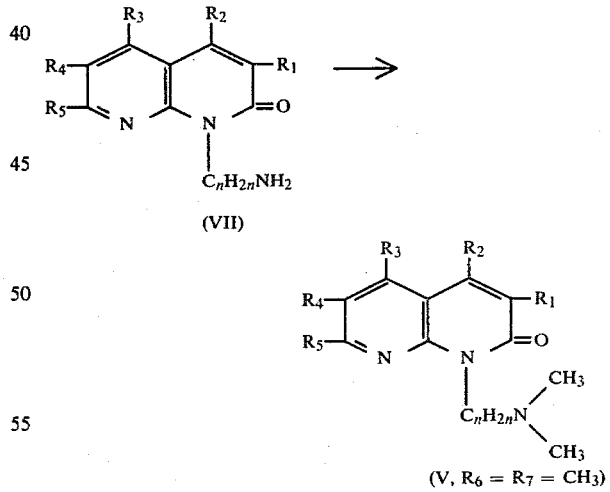

The reaction is carried out in the presence of aqueous formaldehyde and formic acid. The reaction is generally refluxed for from 10 to 30 hours and the product dimethyl compound (V, $R_6=R_7=CH_3$) isolated using known techniques.

An alternate method for the preparation of those compounds where one of $R_6$ and $R_7$ is hydrogen is available where one of $R_6$ and $R_7$ is benzyl.

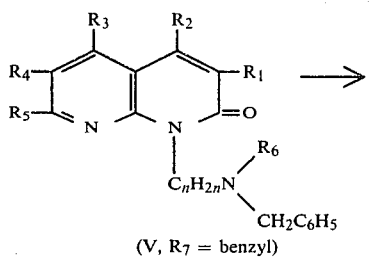

(V, R₇ = benzyl)

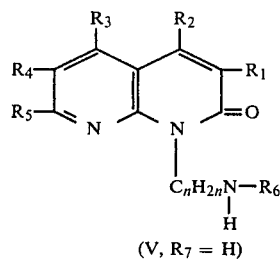

(V, R₇ = H)

The benzyl group is removed by treating compound V ($R_7$=benzyl) with hydrogen generally under pressure of up to about 50 pounds per square inch (although atmospheric hydrogenation is also successful) in the presence of a catalyst such as palladium adsorbed on carbon. The reaction is preferably carried out in a polar solvent such as a lower alkanol. The choice of solvent is not critical so long as the solvent is stable under the reaction conditions employed. Generally the palladium is present on the carbon substrate to the extent of about 5%. The reaction is carried out generally at room temperature although heating to 50° C. is possible. The reaction is complete when a calculated molar equivalent of hydrogen has been reacted as observed by a decrease in the pressure or volume of the hydrogenation apparatus. It is also preferred if the starting material is utilized in the form of the hydrohalic acid addition salt.

The quaternary ammonium salts which form part of this invention are prepared from the compounds of structure V by treatment with a loweralkyl halide.

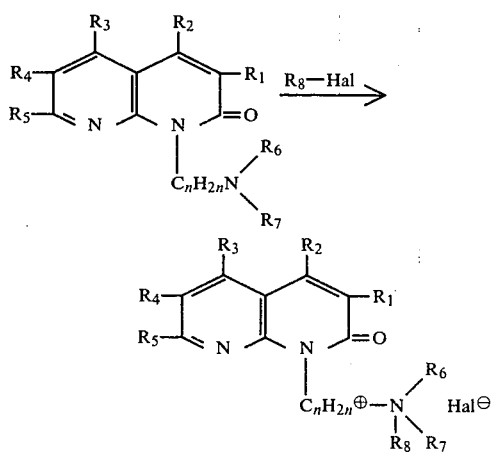

Wherein $R_8$ is loweralkyl and Hal is a halide. The reaction is carried generally in a solvent such as a loweralkanol, preferably ethanol. The reaction mixture is generally stirred at room temperature, higher temperatures are generally not needed, and is complete in about 5 minutes to 1 hour. The product XII is isolated using known techniques.

The compounds of the present invention in the described dosages may be administered orally, however, other routes such as intraperitoneal, subcutaneous, intramuscular or intravenous may be employed.

The active compounds of the present invention are orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suppositories, suspensions, syrups, wafers, chewing gum, and the like. The amount of active compound in such therapeutically useful compositions or preparations is such that a suitable dosage will be obtained.

The tablets, troches, pills, capsules and the like may also contain the following: a binder such as gum tragacanth, acacia, corn starch or gelatin; an excipient such as diacalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type, a liquid carrier such as a fatty oil. Various other materials may be present as coatings or to otherwise modify the physical form of the dosage unit, for instance, tablets, pills or capsules may be coated with shellac, sugar or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

EXAMPLE 1

2-Amino-5,7-diethyl-1,8-naphthyridine

To 50 ml. of 85% phosphoric acid is added with stirring 2,6-diaminopyridine (6.55 g., 0.06 mole) followed by 3,5-heptanedione (7.7 g., 0.06 mole). The mixture is heated on the steam bath under nitrogen atmosphere for 16 hours. The reaction mixture is poured into crushed ice and neutralized with concentrated ammonium hydroxide and extracted with methylene chloride (3×250 ml.). The combined extracts are dried, filtered and concentrated in vacuo. Crystallization of the residue from ethyl acetate affords 2-amino-5,7-diethyl-1,8-naphthyridine melting at 187°–189° C.

EXAMPLE 2

The procedure of Example 1 is followed, using the compounds and reagents listed below to prepare the named naphthyridine compound:

| A. Phosphoric acid (85%) | 100 ml. |
|---|---|
| 2,6-Diaminopyridine | 21.8 g. (0.20 mole) |
| 1,1-Dimethoxy-5-methyl-3-hexanone | 38.4 g. (0.20 mole) |

Affording 2-amino-7-isobutyl-1,8-naphthyridine m.p. 125°–127° C.

| B. | Phosphoric acid (85%) | 75 ml. |
| --- | --- | --- |
| | 2,6-Diaminopyridine | 16.35 g. (0.15 mole) |
| | 1,1-Dimethoxy-3-oxypentane | 21.9 g. (0.15 mole) |

Affording 2-amino-7-ethyl-1,8-naphthyridine m.p. 169.5°–172.5° C.

| C. | Phosphoric acid (85%) | 50 ml. |
| --- | --- | --- |
| | 2,6-Diaminopyridine | 15.0 g. (0.137 mole) |
| | 1,1-Dimethoxy-4-methyl-3-pentanone | 19.5 g. (0.122 mole) |

Affording 2-amino 7-isopropyl-1,8-naphthyridine m.p. 158°–160.5° C.

| D. | Phosphoric acid (85%) | 50 ml. |
| --- | --- | --- |
| | 2,6-Diaminopyridine | 10.9 g. (0.10 mole) |
| | 3-methylpentan-2,4-dione | 11.4 g. (0.10 mole) |

Affording 2-amino-5,6,7-trimethyl-1,8-naphthyridine as a brown solid.

| E. | Phosphoric acid (85%) | 100 ml. |
| --- | --- | --- |
| | 2,6-Diamino-3-phenyl pyridine | 10.7 g. (0.06 mole) |
| | 2,4-pentandione | 6.0 g. (0.06 mole) |

Affording 2-amino-3-phenyl-5,7-dimethyl-1,8-naphthyridine m.p. 191°–195° C.

| F. | Phosphoric acid (85%) | 100 ml. |
| --- | --- | --- |
| | 1,3-Diaminoisoquinoline | 10.0 g. (0.063 mole) |
| | 2,4-Pentanedione | 6.5 g. (0.066 mole) |

Affording 6-amino-1,1-dimethylbenzo[c][1,8]naphthylridine m.p. 253°–260° C.

EXAMPLE 3

2-Amino-5-methyl-7-methoxy-1,8-naphthyridine

To a suspension of 2-acetamido-5-methyl-7-chloro-1,8-naphthyridine (23.5 g., 0.10 mole) in 250 ml. of methanol is added sodium methoxide (16.2 g., 0.30 mole). The resulting solution is stirred at reflux under nitrogen atmosphere for 18 hours. The methanol is removed in vacuo and the residue is taken up in chloroform (250 ml.) and water (100 ml.). The chloroform layer is separated, dried over anhydrous sodium sulfate, filtered and concentrated in vacuo. The residue is recrystallized from ethanol to yield 2-amino-5-methyl-7-methoxy-1,8-naphthyridine melting at 233°–236° C.

EXAMPLE 4

5,7-Diethyl-1,8-naphthyridin-2(1H)-one

To a stirred solution of 2-amino-,5,7-diethyl-1,8-naphthyridine (7.0 g., 0.035 mole) in 45 ml. of trifluoroacetic acid is added sodium nitrite (2.66 g., 0.0385 mole) in small portions over 1 hour at −5° C. The mixture is stirred at −5° C. for 2 hours and for an additional hour at room temperature. The reaction mixture is poured into 300 g. of crushed ice and is made alkaline with a slight excess of concentrated ammonium hydroxide. A yellow solid separates and is filtered and washed with a little ice water. Recrystallization from ethyl acetate affords 5,7-diethyl-1,8-naphthyridin-2-(1H)-one melting at 159°–161° C.

EXAMPLE 5

The procedure of Example 4 is followed, using the compounds and reagents listed below to prepare the named naphthyridine-2-(1H)-one compound.

| A. | Trifluoroacetic acid | 100 ml. |
| --- | --- | --- |
| | Sodium nitrite | 8.3 g. (0.12 mole) |
| | 2-Amino-7-isobutyl-1,8-naphthyridine | 20.1 g. (0.10 mole) |

Affording 7-isobutyl-1,8-naphthyridine-2(1H)-one m.p. 135°–137° C.

| B. | Triflouroacetic acid | 30 ml. |
| --- | --- | --- |
| | Sodium nitrite | 6.55 g. (0.095 mole) |
| | 2-Amino-7-ethyl-1,8-naphthyridine | 13.85 g. (0.08 mole) |

Affording 7-ethyl-1,8-naphthyridine-2(1H)-one m.p. 133°–134.5° C.

| C. | Trifluoroacetic acid | 30 ml. |
| --- | --- | --- |
| | Sodium nitrite | 5.52 g. (0.08 mole) |
| | 2-Amino-7-isopropyl-1,8-naphthyridine | 7.5 g. (0.04 mole) |

Affording 7-isopropyl-1,8-naphthyridine-2(1H)-one

| D. | Trifluoroacetic acid | 50 ml. |
| --- | --- | --- |
| | Sodium nitrite | 6.9 g. (0.10 mole) |
| | 2-Amino-5,6,7-trimethyl-1,8-naphthyridine | 10.0 g. (0.0535 mole) |

Affording 5,6,7-trimethyl-1,8-naphthyridine 2(1H)-one m.p. 170°–175° C.

| E. | Trifluoroacetic acid | 45 ml. |
| --- | --- | --- |
| | Sodium nitrite | 5.3 g. (0.77 mole) |
| | 2-Amino-3-phenyl-5,7-dimethyl-1,8-naphthyridine | 8.6 g. (0.035 mole) |

Affording 3-phenyl-5,7-dimethyl-1,8-naphthyridine-2(1H)-one m.p. 258°–260° C.

| F. | Trifluoroacetic acid | 45 ml. |
| --- | --- | --- |
| | Sodium nitrite | 6.9 g. (0.1 mole) |
| | 6-Amino-1,3-dimethylbenzo[c] [1.8] naphthyridine | 10.0 g. (0.045 mole) |

Affording 1,3-dimethylbenzo[c][1,8]naphthylridine-6(5H)-one m.p. 276°–278° C.

| G. | Trifluoroacetic acid | 60 ml. |
| --- | --- | --- |
| | Sodium nitrite | 11.0 g. (0.16 mole) |
| | 2-Amino-5-methyl-7-methoxy-1,8-naphthyridine | 15.1 g. (0.08 mole) |

Affording 5-methyl-7-methoxy-1,8-naphthyridine-2(1H)-one m.p. 214°–216.5° C.

EXAMPLE 6

1-(2-Dimethylaminoethyl)-5,7-diethyl-1,8-naphthyridin-2(1H)-one

To a suspension of 5,7-diethyl-1,8-naphthyridin-2(1H)-one (4.04 g., 0.02 mole) in 25 ml. of dry dimethylformamide under nitrogen atmosphere is added a 57% suspension of sodium hydride in mineral oil (0.84 g., 0.02 mole). This mixture is stirred at room temperature for 0.5 hours. Then a mixture of 2-dimethylaminoethyl chloride hydrochloride (3.17 g., 0.022 mole) and a 57% suspension of sodium hydride in mineral oil (0.93 g., 0.022 mole) in 25 ml. of dry dimethylformamide is added to the above suspension. The mixture is stirred at steam bath temperature overnight (16 hours). After the mixture is cooled to room temperature it is filtered to remove salt (2.6 g., theory 2.45 g.). Removal of the solvent under reduced pressure gives a pale tan waxy solid (4.8 g.). Several recrystallizations from hexane gives 1-(2-dimethylaminoethyl)-5,7-diethyl-1,8-naphthyridin-2(1H)-one melting at 59.5°–61° C.

alcohol, a solution of the desired acid in a similar solvent.

TABLE I

| | $R_1$ | $R_2$ | $R_3$ | $R_4$ | $R_5$ | A g.(moles) | | B g. (moles) | | C g. (moles) | | D Melting Point (salt) |
|---|---|---|---|---|---|---|---|---|---|---|---|---|
| a | H | H | H | H | isobutyl | 12.1 | (0.06) | 9.36 | (0.065) | 5.27 | (0.125) | 189°–191° C. (HCl) |
| b | H | H | H | H | $CH_3$ | 4.8 | (0.03) | 4.75 | (0.033) | 2.65 | (0.063) | 200°–203.5° C. (HCl) . $H_2O$ |
| c | H | H | H | H | $C_2H_5$ | 10.4 | (0.06) | 10.16 | (0.07) | 5.46 | (0.13) | 146°–149° C. (HCl) $\frac{1}{2}H_2O$ |
| d | H | H | H | $CH_3$ | H | 1.6 | (0.01) | 1.58 | (0.011) | 0.88 | (0.021) | 207°–210° C. (HCl) |
| e | H | H | $CH_3$ | H | H | 4.0 | (0.025) | 4.32 | (0.03) | 2.3 | (0.055) | 228°–230° C. (HCl) |
| f | H | H | $CF_3$ | H | $CF_3$ | 5.64 | (0.02) | 3.6 | (0.025) | 1.89 | (0.045) | 203.5°–206.5° C. (HCl) . $H_2O$ |
| g | H | H | $CF_3$ | H | $CH_3$ | 0.55 | (0.0024) | 0.43 | (0.003) | 0.226 | (0.0054) | 102.5°–103.5° C. $\frac{1}{2}H_2O$ |
| h | H | H | $CH_3$ | H | $CF_3$ | 1.0 | (0.0044) | 0.72 | (0.005) | 0.395 | (0.0094) | 86°–87.5° C. |
| i | H | $CH_3$ | H | H | $NH_2$ | 14.0 | (0.08) | 11.5 | (0.08) | 6.74 | (0.16) | 168°–172° C. |
| j | H | H | H | H | $NH_2$ | 12.9 | (0.08) | 11.5 | (0.08) | 6.74 | (0.16) | 134.5°–137° C. |
| k | H | H | H | H | $CH(CH_3)_2$ | 9.4 | (0.05) | 7.92 | (0.055) | 4.42 | (0.105) | 207°–210.5° C. (HCl) |
| l | H | H | $CH_3$ | $CH_3$ | $CH_3$ | 5.3 | (0.028) | 4.04 | (0.028) | 2.36 | (0.056) | 180°–185° C. (HCl) . $H_2O$ |
| m | H | H | $CH_3$ | H | —$OCH_3$ | 11.4 | (0.06) | 8.65 | (0.06) | 5.06 | (0.12) | 98.5°–101.5° C. |
| n | H | H | H | H | H | 2% | (0.02) | 2.9 | (0.02) | 1.7 | (0.041) | 202°–203° C. (HCl) |

EXAMPLE 7

The procedure of Example 6 is followed to prepare other 1-substituted naphthyridine-2(1H)-ones according to the following reaction scheme:

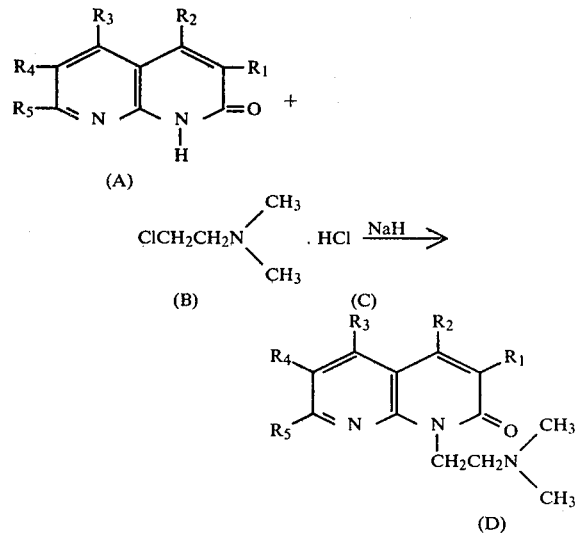

The substituent groups and the quantities of each reagent and compound employed are set forth in Table I.

In Table I, where the product is indicated as being isolated as a salt, such salt is prepared by adding to a solution of the free base in a suitable solvent, such as an

EXAMPLE 8

A.
1-(2-Diethylaminoethyl)-5,7-dimethyl-1,8-naphthyridin-2(1H)-one Hydrochloride 5,7-Dimethyl-1,8-naphthyridin-1,8-naphthyridin-2(1H)-one(3.48 g., 0.02 mole) is added to a solution of sodium ethoxide made by disolving sodium pellets (1.0 g., 0.043 mole) in 50 ml. of ethanol. The mixture is heated to reflux and a solution of 2-diethylaminoethyl chloride hydrochloride (3.44 g., 0.02 mole) in 50 ml. of absolute ethanol is added in a dropwise manner. Heating under reflux is continued for six hours, the mixture is cooled, filtered and evaporated under reduced pressure. The residue is dissolved in ether and extracted with dilute hydrochloric acid. The acidic extract is filtered through charcoal and made basic with saturated sodium carbonate solution. The product is extracted into ether, containing the free base of the title compound, is dried with anhydrous sodium sulfate and the hydrochloride salt is prepared by addition of ethereal hydrogen chloride. The salt is collected and recrystallized from isopropanol to yield 3.56 g. of 1-(2-diethylaminoethyl)-5,7-dimethyl-1,8-naphthyridin-2(1H)-one hydrochloride with a m.p. of 226°–228° C.

B.
1-(2-Dimehylaminoethyl)-5,7-dimethyl-1,8-naphthyridine-2(1H)-one

Following the above procedure employing dimethylamino ethyl chloride hydrochloride as the alkylating reagent, there is obtained 1-(2-dimethylaminoethyl)-5,7-dimethyl-1,8-naphthyridine-2(1H)-one.

EXAMPLE 9

The procedure of Example 8 is followed to prepare the 1-substituted naphthyridin-2(1H)-ones according to the following reaction scheme:

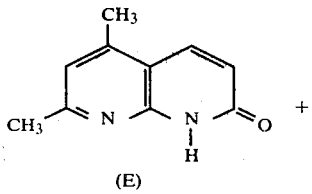

-continued

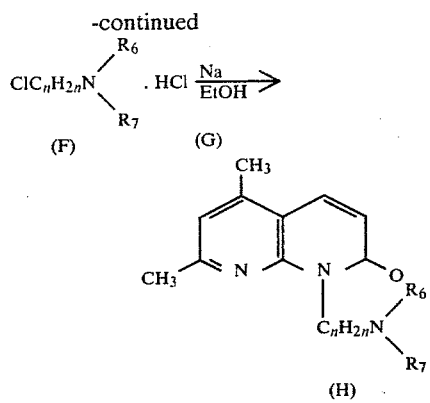

The substituent groups and the quantities of each reagent and compound employed are set forth in Table II.

In parts (d) and (h) of Table II the "pyrrolidinyl" and "2,2,6,6-tetramethylpiperidins" designations for $R_6$ and $R_7$ indicate that the named groups include the nitrogen atoms to which $R_6$ and $R_7$ are attached.

In part e of Table II the value of "3" for n indicates a propylene group.

In part g of Table II the value of "4" for n indicates a "2-methylpropylene" group.

In parts g and h of Table II the acid addition salt is not prepared, thus the procedure of Example 8 describing the acidification of the ether solution is omitted.

TABLE II

| | $R_6$ | $R_7$ | n | E g.(moles) | | F g.(moles) | | G(Na) g.(moles) | | H Melting Point (salt) |
|---|---|---|---|---|---|---|---|---|---|---|
| a | n-butyl | n-butyl | 2 | 2.6 | (0.015) | 3.4 | (0.015) | 0.75 | (0.033) | 195°–197° C. (HCl) . ½H₂O |
| b | isopropyl | isopropyl | 2 | 3.5 | (0.02) | 4.0 | (0.02) | 1.0 | (0.043) | 261°–262° C. (HCl) |
| c | cyclohexyl | cyclohexyl | 2 | 2.6 | (0.015) | 4.2 | (0.015) | 0.75 | (0.033) | 259°–260° C. (HCl) |
| d | pyrrolidinyl | | 2 | 3.5 | (0.02) | 3.4 | (0.02) | 1.0 | (0.043) | 216°–217° C. (HCl) |
| e | methyl | methyl | 3 | 3.5 | (0.02) | 3.2 | (0.02) | 1.0 | (0.043) | 232°–234° C. (HCl) |
| f | benzyl | methyl | 2 | 15.7 | (0.09) | 19.8 | (0.09) | 4.5 | (0.019) | 208°–210° C. (HCl) |
| g | methyl | methyl | 4 | 10.8 | (0.06) | 12.9 | (0.075) | 3.4 | (0.015) | 109°–111° C. |
| h | 2,2,6,6-tetramethylpiperidino | | 2 | 2.6 | (0.015) | 3.6 | (0.015) | 0.75 | (0.033) | 170°–172° C. |

EXAMPLE 10

The procedure of Example 8 is followed using the compounds and reagents listed below in ethanol to prepare the named naphthyridin-one compounds:

| A. | Sodium | 1.34 g. (0.058 mole) |
|---|---|---|
| | Dimethylaminoethylchloride hydrochloride | 4.15 g. (0.029 mole) |
| | 3-Phenyl-5,7-dimethyl-1,8-naphthyridin-2(1H)-one | 6.0 g. (0.024 mole) |

Affording 1-(2-dimethylaminoethyl)-3-phenyl-5,7-dimethyl-1,8-naphthyridin-2(1H)-one m.p. 135°–137° C.

| B. | Sodium | 1.34 g. (0.058 mole) |
|---|---|---|
| | Dimethylaminoethylchloride hydrochloride | 4.15 g. (0.029 mole) |
| | 1,3-Dimethylbenzo[c][1,8]naphthyridin-6(5H)-one | 5.38 g. (0.024 mole) |

Affording 5-dimethylaminoethyl-1,3-dimethylbenzo[c][1,8]naphthyridin-6[5H]-one m.p. 128.5°–130.5° C.

EXAMPLE 11

A.

1-(2-Phthalimidoethyl)-5,7-dimethyl-1,8-naphthyridin-2(1H)-one

To a suspension of 5,7-dimethyl-1,8-naphthyridin-2(1H)-one (3.5 g., 0.02 mole) in 25 ml. of dry dimethyl formamide under nitrogen atmosphere is added a 57% suspension of sodium hydride in mineral oil (0.84 g., 0.02 mole). This mixture is stirred at room temperature for ½ hour. A mixture of N-(2-chloroethyl) phthalimide (4.6 g., 0.022 mole) in 25 ml. of dry dimethylformamide is added to the first suspension. The mixture is stirred at steam bath temperature for 16 hours. On cooling, it is filtered to remove salt and the filtrate evaporated to dryness in vacuo to afford 1-(2-phthalimidoethyl)-5,7-dimethyl-1,8-naphthyridin-2(1H)-one.

B.

1(4-Phthalimidobutyl)-5,7-dimethyl-1,8-naphthyridin-2-(1H)-one

The above procedure is employed with equimolar quantities of N-(4-chlorobutyl) phthalimide, to prepare 1(4-phthalimidobutyl)-5,7-dimethyl-1,8-naphthyridin-2(1H)-one.

EXAMPLE 12

A.

1-(2-Aminoethyl)-5,7-dimethyl-1,8-naphthyridin-2(1H)-one Hydrochloride

A mixture of 1-(2-phthalimidoethyl)-5,7-dimethyl-1,8-naphthyridin-2(1H)-one (5.2 gm., 0.015 mole) and 95% hydrazine (1.8 ml., 0.053 mole) in absolute ethanol (50 ml.) is refluxed for one hour. The reaction is cooled, water (37.8 ml.) and concentrated hydrochloric acid (37.5 ml.) are added. After refluxing for one half hour, the mixture is cooled in an ice bath and phthalhydrazide (2.85 gm., 0.0125 mole) is filtered off. The filtrate is concentrated and the residue is dissolved in water, made basic with saturated sodium carbonate and extracted with methylene chloride. The organic layer is dried over anhydrous sodium sulfate, filtered and evaporated. The residue containing the free base of the title compound is dissolved in a minimum amount of methanol and treated with ethereal hydrogen chloride. Recrystallization of the product from isopropanol gives 1-(2-aminoethyl)-5,7-dimethyl-1,8-naphthyridine-2(1H)-one hydrochloride melting at 253.5°–254.5° C.

B.

1-(4-Aminobutyl)-5,7-dimethyl-1,8-naphthyridine-2(1H)-Hydrochloride

The above procedure is employed with equimolar quantities of 1-(4-phthalimidobutyl)-5,7-dimethyl-1,8- naphthyridine-2(1H)-one to prepare 1-(4-aminobutyl)-5,7-dimethyl-1,8-naphthyridine-2(1H)-one hydrochloride m.p. 188°–190° C. or the free base of such compound.

EXAMPLE 13

A.

1-{2-[(N-methylthiocarbamoyl)amino]ethyl}-5,7-dimethyl-1,8-naphthyridin-2(1H)-one A mixture of the free base of 1-(2-aminoethyl)-5,7-dimethyl-1,8-naphthyridin-2(1H)-one (700 mg., 0.0032 mole) as prepared in Example 12 and methyl isothiocyanate (180 mg., 0.004 mole) in 5 ml. of water is heated at reflux for 30 minutes. On cooling the reaction, the product is collected by filtration. After recrystallization from methanol, 1-{2-[(N-methylthiocarbamoyl)amino]ethyl}-5,7-dimethyl-1,8-naphthyridin-2(1H)-one m.p. 216.5°–218° C. is obtained.

B.

1-{4-[(N-methylthiocarbamoyl)amino]butyl}-5,7-dimethyl-1,8-naphthyridine-2(1H)-one The above procedure is employed with equimolar quantities of 1-(4-aminobutyl)-5,7-dimethyl-1,8-naphthyridin-2(1H)-one to prepare 1-{4-[(N-methylthiocarbamoyl)amino]butyl}-5,7-dimethyl-1,8-naphthyridin-2(1H)-one m.p. 147°–149° C.

EXAMPLE 14

1-(2-Methylaminoethyl)-5,7-dimethyl-1,8-naphthyridin-2(1H)-one Hydrochloride

1(2-Benzylmethylaminoethyl)-5,7-dimethyl-1,8-naphthyridin-2(1H)-one hydrochloride (8.56 g., 0.024 mole) is dissolved in 80 ml. of ethanol, 5% palladium on carbon (0.8 g.) catalyst is added and the mixture is hydrogenated at a pressure of 45 lbs. per sq. inch until hydrogen is no longer taken up. The mixture is filtered concentrated under reduced pressure and the residue is crystallized from isopropanol. 1-(2-Methylaminoethyl)-5,7-dimethyl-1,8-naphthyridin-2(1H)-one hydrochloride having a melting point of 106°–109° C. is obtained.

EXAMPLE 15

1-(4-Dimethylaminobutyl)-5,7-dimethyl-1,8-naphthyridin-2(1H)-one Dihydrobromide

Formic acid (10 ml., 0.265 mole) is added with stirring at 5° C. in 1 ml. portions to 1-(4-aminobutyl)-5,7-dimethyl-1,8-naphthyridin-2-(1H)-one (13.7 g., 0.056 mole) (obtained as the free base from Example 12B). Formaldehyde (37%, 10 ml.) is added to the semi-solid mass and the mixture is refluxed for 18 hours. On cooling, hydrochloric acid (12 N, 13.7 ml.) is added and the mixture concentrated under vacuum. The residue is dissolved in water and the solution is made alkaline with excess sodium hydroxide. The product is extracted into diethyl ether. The ethereal solution is dried over sodium sulfate and filtered. Aqueous hydrobromic acid is added to the filtrate and the mixture concentrated under vacuum. The residue is recrystallized from ethanolethyl ether to yield 1-(4-dimethylaminobutyl)-5,7-dimethyl-1,8-naphthyridin-2(1H)-one dihydrobromide melting at 222°–225° C.

EXAMPLE 16

N-{[1,2-Dihydro-2-oxo-5,7-dimethyl-1-(1,8-naphthyridyl)]ethyl}-N,N,N-trimethylammonium Iodide Methyl iodide (1,7 g., 0.012 mole) is added to a solution of 1-(2-dimethylaminoethyl)-5,7-dimethyl-1,8-naphthyridin-2(1H)-one (2.45 g., 0.01 mole) (obtained as the free base from Example 8B) in 10 ml. of absolute ethanol and the mixture is stirred for 20 minutes. Ethyl ether is added and the precipitated product is filtered and recrystallized from methanol/ethyl ether to give N-{[1,2-dihydro-2-oxo-5,7-dimethyl-1-(1,8-naphthyridyl)]ethyl}-N,N,N-trimethylammonium iodide with a melting point of 219°–220° C.

EXAMPLE 17

1-(2-Dimethylaminoethyl)-5,7-dimethyl-3,4-dihydro-1,8-naphthyridin-2(1H)-one Dihydrobromide A solution of 1-(2-dimethylaminoethyl)-5,7-dimethyl-1,8-naphthyridin-2(1H)-one hydrochloride (2.82 g., 0.01 mole) in 35 ml. of glacial acetic acid containing 300 mg. of platinum oxide is hydrogenated at atmospheric pressure until 0.01 mole of hydrogen is taken up. The mixture is filtered, the solvent is evaporated and the residue is dissolved in water. After filtration through charcoal, the solution is made basic with sodium carbonate, and the free base of the title product is extracted with ethyl ether. An ethereal solution of hydrogen bromide is added and the precipitate is recrystallized from methanolethyl ether to yield 1-(2-dimethylaminoethyl)-5,7-dimethyl-3,4-dihydro-1,8-naphthyridin-2(1H)-one dihydrobromide with a melting point of 218°–221° C.

EXAMPLE 18

The procedure of Example 17 may be employed to reduce other naphthyridin-2(1H)-ones to the corresponding 3,4-dihydronaphthyridin-2(1H)-ones. By following said hydrogenation procedure the products listed below are obtained:

A. 1-(2-Dimethylaminoethyl)-7-ethyl-3,4-dihydro-1,8-naphthyridin-2(1H)-one hydrochloride
B. 1-(4-Dimethylaminobutyl)-5,7-dimethyl-3,4-dihydro-1,8-naphthyridin-2(1H)-one
C. 1-(2-Aminoethyl)-5,7-dimethyl-3,4-dihydro-1,8-naphthyridin-2(1H)-one hydrobromide
D. 1-(2-Dimethylaminoethyl)-5-methyl-7-methoxy-3,4-dihydro-1,8-naphthyridin-2(1H)-one
E. 1-(2-Methylaminoethyl)-5,7-dimethyl-3,4-dihydro-1,8-naphthyridine-2(1H)-one hydrochloride.
F. 1-(2-Dimethylaminoethyl)-7-amino-3,4-dihydro-1,8-naphthyridin-2(1H)-one dihydrochloride.

The compounds prepared by this procedure may be isolated as the free base, such as compound B or as the acid addition salt which are prepared by the procedure described in Example 17.

EXAMPLE 19

1-(2-Dimethylaminoethyl)-5,7-dimethyl-1,8-naphthyridin-2(1H)-thione Hydrochloride A mixture of 1-(2-dimethylaminoethyl)-5,7-dimethyl-1,8-naphthyridin-2(1H)-one (2.5 g., 0.01 mole) and phosphorus pentasulfide (2.0 g., 0.009 mole) in 60 ml. of methylene chloride is heated at reflux for 4 hours. The reaction is cooled, water and solid potassium carbonate added, and the organic layer is separated, dried, filtered through charcoal and evaporated to dryness. The residue is dissolved in ether, hydrogen chloride is added and the salt is recrystallized from isopropanol to yield 1-(2-dimethylaminoethyl)-5,7-dimethyl-1,8-naphthyridin-2(1H)-thione hydrochloride m.p. 209°–211° C.

EXAMPLE 20

The procedure of Example 19 is followed to prepare other naphthyridin-2(1H) thiones according to the following reaction scheme:

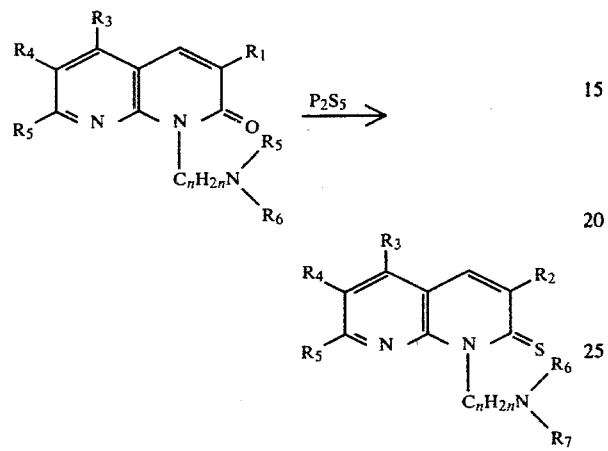

In item g of Table III the value of 4 for n indicates the 2-methylpropylene group.

TABLE III

| | $R_1$ | $R_3$ | $R_4$ | $R_5$ | $R_6$ | $R_7$ | n |
|---|---|---|---|---|---|---|---|
| a | H | H | H | $CH_3$ | $CH_3$ | $CH_3$ | 2 |
| b | H | $CH_3$ | H | H | $CH_3$ | $CH_3$ | 2 |
| c | H | $C_2H_5$ | H | $C_2H_5$ | $CH_3$ | $CH_3$ | 2 |
| d | $C_6H_5$ | $CH_3$ | H | $CH_3$ | $CH_3$ | $CH_3$ | 2 |
| e | H | $CH_3$ | H | $CH_3$ | $CH(CH_3)_2$ | $CH(CH_3)_2$ | 2 |
| f | H | $CH_3$ | H | $CH_3$ | —$(CH_2)_4$— | | 2 |
| g | H | $CH_3$ | H | $CH_3$ | $CH_3$ | $CH_3$ | 4 |
| h | H | H | $CH_3$ | H | $CH_3$ | $CH_3$ | 2 |

What is claimed is:

1. A compound having the formula:

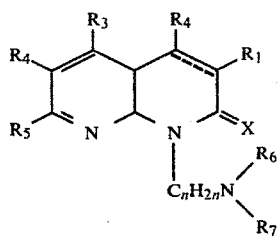

wherein
X is oxygen;
n is an integer of from 2 to 6 such that the length of the carbon chain connecting the two nitrogen atoms is not less than 2;
$R_1$, $R_2$, $R_3$, $R_4$ and $R_5$ are independently hydrogen, loweralkyl, loweralkoxy, amino, haloloweralkyl, or phenyl; or any two adjacent substituents may be joined to form a benzo substituent;
$R_6$ and $R_7$ are independently N-loweralkylthiocarbamoyl; or $R_6$ and $R_7$ may be joined to form a morpholino ring or $R_6$ and $R_7$ may be an alkylene linkage of 4 or 5 carbon atoms to form a pyrrolidine or piperidine group which may be substituted with loweralkyl, oxo or benzo substituents;
and the broken line in the 3,4 position of the naphthyridine molecule indicates that the bond may be either a single or a double bond;
and the acid addition and quaternary ammonium salts thereof;
and those compounds wherein
X is sulfur,
n is an integer of from 2 to 6 such that the length of the carbon chain connecting the two nitrogen atoms is not less than 2;
$R_1$, $R_2$, $R_3$, $R_4$ and $R_5$ are independently hydrogen, loweralkyl, loweralkoxy, amino, haloloweralkyl, or phenyl; or any two adjacent substituents may be joined to form a benzo substituent;
$R_6$ and $R_7$ are independently hydrogen, phenylloweralkyl, N-loweralkylcarbamoyl, N-loweralkylthiocarbamoyl; or $R_6$ and $R_7$ may be joined to form a morpholino ring or $R_6$ and $R_7$ may be an alkylene linkage of 4 or 5 carbon atoms to form a pyrrolidine or piperidine group which may be substituted with loweralkyl, oxo or benzo substituents;
and the broken line in the 3,4 position of the naphthyridine molecule indicates that the bond may be either a single or a double bond;
and the acid addition and quaternary ammonium salts thereof.

2. The compound of claim 1 which is 1-(2-pyrrolidinylethyl)-5,7-dimethyl-1,8-naphthyridin-2(1H)one.

3. The compound of claim 1 which is 1-(2,2,6,6-tetramethylpiperidino)-5,7-dimethyl-1,8-naphthyridin-2(1H)one.

4. The compound of claim 1 which is 1- or 2-[(N-methylthiocarbamoyl)amino]ethyl-5,7-dimethyl-1,8-naphthyridin-2(1H)one.

5. The compound of claim 1 which is 1- 4-[(N-methylthiocarbamoyl)amino]butyl]-5,7-dimethyl-1,8-naphthyridine-2(1H)one.

6. The compound of claim 1 which is 1-(2-dimethylaminoethyl)-5,7-dimethyl-1,8-naphthyridin-2(1H) thione.

7. A method for the suppression of gastric acid secretions which comprises administering to an animal with excess gastric acid secretions, an effective amount of a compound of claim 1.

* * * * *